United States Patent [19]
Takano et al.

[11] Patent Number: 5,973,196
[45] Date of Patent: Oct. 26, 1999

[54] PROCESS FOR PRODUCING PURIFIED TEREPHTHALIC ACID

[75] Inventors: Toshinori Takano, Saeki-Gun; Hiroshi Suzuki, Ohtake; Norio Taniguchi, Iwakuni, all of Japan

[73] Assignee: Mitsui Chemicals, Inc., Tokyo, Japan

[21] Appl. No.: 09/024,980

[22] Filed: Feb. 17, 1998

[30] Foreign Application Priority Data

Feb. 17, 1997 [JP] Japan ................................ 9-032375

[51] Int. Cl.⁶ .................................................. C07C 51/42
[52] U.S. Cl. ........................................... 562/485; 562/486
[58] Field of Search ..................................... 562/486, 485

[56] References Cited

U.S. PATENT DOCUMENTS

| | | | |
|---|---|---|---|
| 5,557,009 | 9/1996 | Izumisawa et al. | 562/486 |
| 5,741,927 | 4/1998 | Parker et al. | 562/468 |

FOREIGN PATENT DOCUMENTS

| | | |
|---|---|---|
| 0265137A | 4/1988 | European Pat. Off. . |
| 0469327A | 2/1992 | European Pat. Off. . |
| 466553 | 3/1992 | Japan . |

*Primary Examiner*—Paul J. Killos
*Assistant Examiner*—J. Parsa
*Attorney, Agent, or Firm*—Birch, Stewart, Kolasch & Birch, LLP

[57] ABSTRACT

A process for producing purified terephthalic acid capable of controlling the transmittance of the purified terephthalic acid product promptly in a simple procedure without necessitating to alter the condition of the oxidation of paraxylene to thereby permit a minute control of the process and to allow to obtain a purified terephthalic acid product with a low and constant impurity level within a certain range, which process comprises hydrogenating a crude terephthalic acid resulting from a liquid phase oxidation of paraxylene in a hydrogenation reactor 6 in the presence of a hydrogenation catalyst, followed by precipitation of the crystals 8, a solid/liquid separation 11, re-slurrying 14 of the separated crystals in water and a further solid/liquid separation 16, to obtain a purified terephthalic acid; observing the transmittance of the resulting purified terephthalic acid; and controlling the temperature of the washing water so as to maintain the observed transmittance within a predetermined range.

10 Claims, 1 Drawing Sheet

PROCESS FOR PRODUCING PURIFIED TEREPHTHALIC ACID

FIELD OF THE INVENTION

The present invention relates to a process for producing a purified terephthalic acid (PTA) by hydrogenating a crude terephthalic acid (CTA) obtained by liquid phase oxidation of paraxylene.

DESCRIPTION OF THE RELATED TECHNIQUES

On oxidizing paraxylene with a molecular oxygen-containing gas in liquid phase, a crude product of terephthalic acid is formed, which contains, as a main impurity component, 4-carboxybenzaldehyde (abbreviated hereinafter as 4-CBA), in addition to terephthalic acid. It is necessary to purify such a crude terephthalic acid in using as a starting material for producing polyester fiber, which require a purified terephthalic acid as a starting material.

For producing a purified terephthalic acid, a process is known in which a crude terephthalic acid is treated by hydrogenation in the presence of a hydrogenation catalyst (Cf., for example, Japanese Patent Kokai Hei 4-66553 A). In this process, a purified terephthalic acid is produced by reducing 4-CBA into paratoluic acid, which is water-soluble, by hydrogenation and removing it from terephthalic acid by, for example, solid/liquid separation after crystallization of terephthalic acid.

The above-mentioned treatment by hydrogenation is realized by arranging a fixed layer of a solid catalyst within a reactor and passing an aqueous solution of the crude terephthalic acid to the catalyst layer while supplying hydrogen gas to the reactor. The 4-CBA existing in the crude terephthalic acid is reduced thereby into paratoluic acid. When the reaction mixture is cooled, terephthalic acid crystals will precipitate, while most of the impurities, such as paratoluic acid etc., remain dissolved in the mother liquor. By performing a solid/liquid separation, a primary purified product of terephthalic acid crystals having some inclusion of mother liquor adhered on the crystals is obtained, while most of the impurities are left dissolved in the separated mother liquor.

By washing out the rest of the impurities adhered on the crystals, a purified terephthalic acid is obtained. A commonly employed washing technique consists in a re-slurrying the crystals of the primary product in water, in order to transfer the impurities adhered on the crystals to the aqueous layer. By effecting a solid/liquid separation of the resulting slurry again, almost all the impurities are retained in the liquid phase and a highly purified terephthalic acid having scarce impurity content is obtained.

For such a purified terephthalic acid to be used as the starting material for polyester fibers and so on, it is required to maintain a constant quality and, thus, a constant impurity level, in addition to the requirement for high purity. A purified terephthalic acid may contain small amount of contaminants, such as paratoluic acid resulting from the reduction of 4-CBA, and others. The amount of the contaminants can be assessed by observing transmittance of the purified terephthalic acid as a substitute parameter.

The amount of the impurities in the purified terephthalic acid may vary with the amount of the impurities in the starting crude terephthalic acid to be treated by hydrogenation. It has heretofore been practised to maintain the amount of impurities in the crude terephthalic acid within a certain range mainly by controlling the condition in the process for the production of the crude terephthalic acid, namely, by controlling the condition of oxidation of paraxylene.

However, a control of the impurity level in the crude terephthalic acid by adjusting the oxidation condition has a difficulty that a prompt response to the optimum condition is not able due to a considerable time lag required for the actual appearance of influence on the amount of impurities in the purified product, so that it is not adapted for a minute administration of the product quality.

SUMMARY OF THE INVENTION

An object of the present invention is to provide a process for producing purified terephthalic acid which can afford to control the transmittance of the purified terephthalic acid product promptly by a simple procedure without altering the condition of oxidation of paraxylene, whereby a minute control of production can be realized and a purified product of terephthalic acid having a constant impurity level can be produced.

The process for producing purified terephthalic acid according to the present invention comprises hydrogenating a crude terephthalic acid obtained by a liquid phase oxidation of paraxylene in the presence of a hydrogenation catalyst, causing crystals of terephthalic acid to precipitate out of the hydrogenation reaction liquor, separating the resulting crystals from the mother liquor, washing the separated crystals with water, observing the transmittance of the resulting purified terephthalic acid and controlling the temperature of the washing water so as to maintain the observed transmittance within a predetermined range.

DETAILED DESCRIPTION OF THE DISCLOSURE

Figure 1:
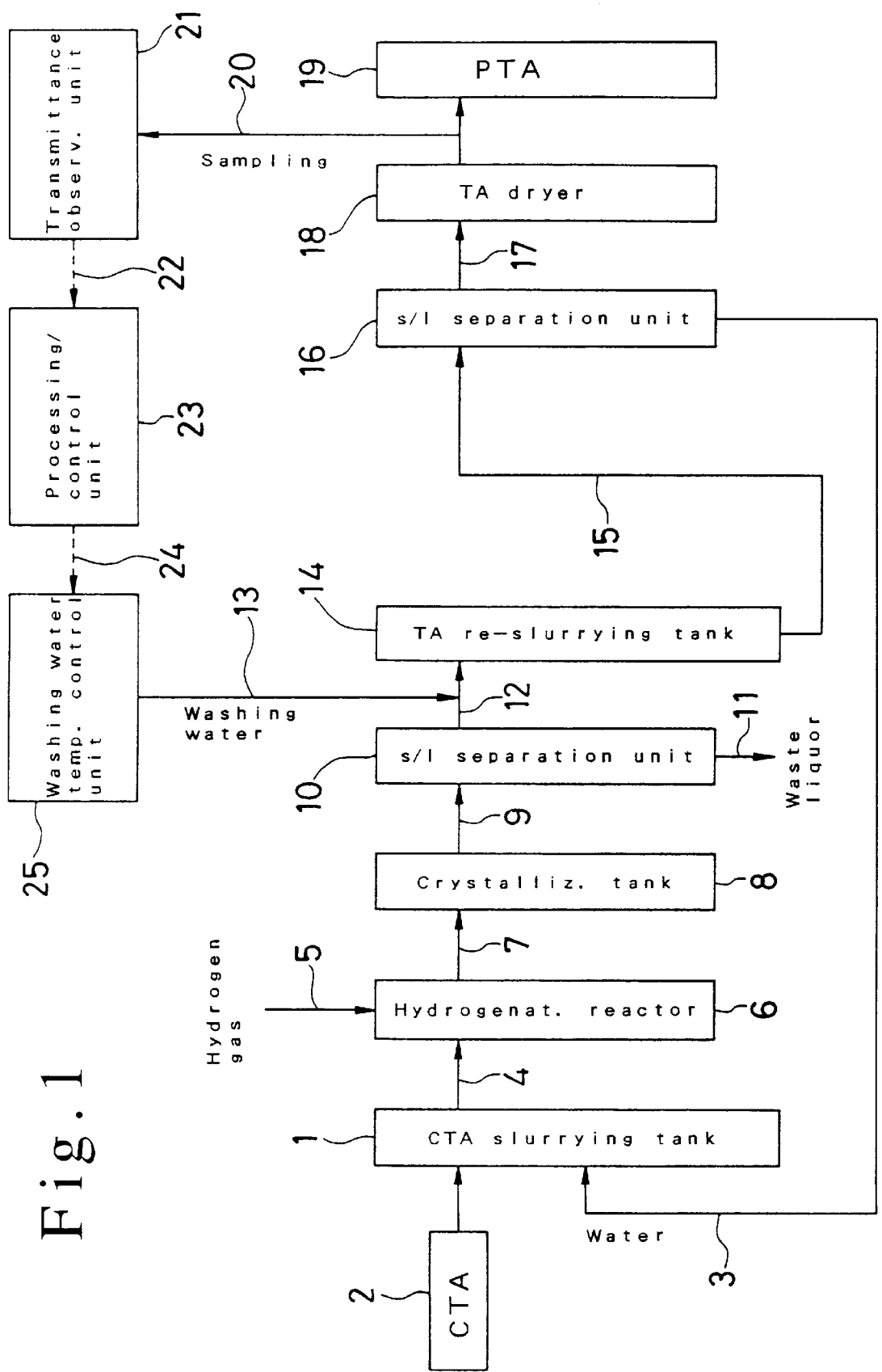
FIG. 1 shows a flow sheet of an embodiment of the process for producing purified terephthalic acid according to the present invention.

The crude terephthalic acid to be treated by hydrogenation according to the present invention is that obtained by a liquid phase oxidation of paraxylene. Such a crude product of terephthalic acid may, in general, contain, as a principal impurity, 4-CBA in an amount of about 0.1–0.4% by weight.

The liquid phase oxidation of paraxylene is realized in a reaction solvent using an oxidation catalyst. As the solvent for the liquid phase oxidation of paraxylene, there may be used, for example, a fatty acid, such as acetic acid, propionic acid, n-butyric acid, isobutyric acid, n-valeric acid, trimethylacetic acid or caproic acid, or a mixture of such an acid with water. Among them, a solvent of acetic acid or of acetic acid containing water is preferred, as described afterwards.

As the catalyst of liquid phase oxidation of paraxylene, there may generally be employed a heavy metal compound and/or a bromine-containing compound, wherein, as the former, a compound of nickel, cobalt, iron, chromium, manganese or the like is enumerated and wherein both are employed as the element or as a compound preferably in a form soluble in the reaction system. In a preferred mode of the catalyst, cobalt compound, manganese compound and bromine compound are used. Cobalt compound may be used usually in an amount of 10–10,000 ppm, preferably 100–3,000 ppm, calculated as cobalt, based on the weight of the reaction solvent. The proportion of the manganese compound to the cobalt compound may be in the range of 0.001–2 as the atomic ratio of manganese to cobalt. The proportion of the bromine compound to the cobalt compound may be in the range of 0.1–5 as the atomic ratio of bromine to cobalt.

The liquid phase oxidation of paraxylene is carried out using a molecular oxygen-containing gas. For such a molecular oxygen-containing gas, usually a gas composed of an oxygen gas diluted by an inert gas, such as the atmospheric air or oxygen-enriched air, may be used. The oxidation reaction is effected usually at a temperature in the range of 150–270° C., preferably 170–220° C., under a pressure at which the reaction mixture can be maintained in the liquid phase and usually in the range of 0.5–4 MPa (gauge). The duration of the oxidation reaction may usually be in the order of 20–180 minutes as the residence time in the reactor, though variable in accordance with the size of the reactor and other parameters. The water content in the reaction system may usually be in the range of 3–30% by weight, preferably 5–15% by weight.

According to the present invention, the crude terephthalic acid obtained from the liquid phase oxidation of paraxylene is subjected to a treatment by hydrogenation in a hydrogenation reactor in the presence of a hydrogenation catalyst. Here, the crude terephthalic acid separated from the mother liquor of the liquid phase oxidation is re-slurried in water and the resulting aqueous slurry is heated and pressurized to form an aqueous solution of terephthalic acid, which is introduced into the hydrogenation reactor and is subjected to hydrogenation. For the hydrogenation reactor, there is no special limitation in the form and construction thereof, so long as it permits to arrange therein a catalyst layer filled with a hydrogenation catalyst and allows supply of hydrogen gas thereto to effect contact of the aqueous solution of terephthalic acid and hydrogen with the catalyst.

For the hydrogenation reactor, one which has a fixed layer of solid catalyst disposed therein, a supply line for supplying the aqueous terephthalic acid solution thereto, a discharge line for discharging the treated liquor therefrom and a feed line for feeding hydrogen gas thereto is preferable. While the aqueous solution of terephthalic acid may be supplied so as to cause an upflow in the reactor, it is preferable to arrange the aqueous terephthalic acid solution supply line at the top of the reactor and the treated liquor discharge line at the bottom thereof so as to cause a downflow of the aqueous solution in the reactor. Here, hydrogen gas feed line may preferably be disposed at an upper portion of the reactor so as to be introduced therein from above.

While a hydrogenation catalyst conventionally employed hitherfor can be used here, such as for example, palladium, ruthenium, rhodium, osmium, iridium, platinum, platinum black, palladium black, iron and cobalt-nickel, there may be used favorably a solid catalyst, in which such a catalyst as above is supported on a carrier, preferably on an adsorptive carrier, such as activated carbon, so as to permit to build up a fixed layer.

In a steady state, the hydrogenation treatment is realized by first re-slurrying the crude terephthalic acid crystals in water at a concentration of 10–40% by weight, preferably 24–30% by weight, heating the resulting aqueous slurry at a temperature of 230° C. or higher, preferably 240–300° C., under a pressure of 1–11 MPa, preferably 3–9 MPa (gauge), to dissolve the crude terephthalic acid crystals and, then, supplying the resulting aqueous solution of terephthalic acid to the hydrogenation reactor so as to pass it through the solid catalyst layer, while feeding hydrogen gas to the reactor at a feed rate of at least 1.5 molar times, preferably at least 2 molar times the 4-CBA present in the aqueous crude terephthalic acid solution. The hydrogenation is effected at a temperature of 230° C. or higher, preferably 255–300° C., under a pressure of 1–11 MPa, preferably 3–9 MPa (gauge), at a hydrogen partial pressure in the order of at least 0.05 MPa, preferably 0.05–2 MPa.

By the hydrogenation treatment, the 4-CBA present in the crude terephthalic acid is reduced into paratoluic acid which is water-soluble at lower temperatures. Thus, by cooling the hydrogenation treated liquor down to a temperature of 300° C. or lower, preferably 100–280° C., only terephthalic acid crystals will be precipitated, so that paratoluic acid can be separated from terephthalic acid crystals by effecting a solid/liquid separation. The so-separated terephthalic acid crystals have inclusion of impurities of the rest of mother liquor adhered on the crystals and, by washing out the impurities from the crystals, a purified terephthalic acid is obtained.

The washing of the resulting terephthalic acid crystals is effected with water (usually with pure water) to remove the impurities adhered on the crystals. As a concrete technique for the washing, generally a method is employed in which the crystals of primarily purified terephthalic acid resulting from the solid/liquid separation after the crystallization of terephthalic acid are re-slurried in the washing water to transfer the impurities adhered on the crystals to the liquid phase of washing water and subjecting the resulting aqueous slurry again to a solid/liquid separation, whereupon the separated crystals are dried to obtain a purified terephthalic acid product having a low impurity level.

For other washing techniques, there may be exemplified a method, in which a washing liquid is sprayed onto a moving layer of the terephthalic acid crystals separated by a solid/liquid separation on a rotary filter or a centrifuge so as to effect repeated re-slurrying and solid/liquid separation, or a method, in which the reaction solvent is replaced with a washing water by bringing a moving layer of the terephthalic acid crystals separated by a solid/liquid separation on a rotary filter or a centrifuge into contact with the washing water in a counter flow, as disclosed in Japanese Patent Kokai Hei-7-149690 A.

In employing either one of the above washing techniques, a purified terephthalic acid product is obtained by finally effecting a solid/liquid separation and drying, wherein the transmittance of the dried final purified terephthalic acid crystals is observed to ascertain the product quality by sampling it. The observation of the transmittance is realized in general by dissolving the sample crystals in an alkaline water and determining the transmittance of the solution on a spectrophotometer at a wave length of 340 nm or 400 nm.

According to the present invention, the temperature of the washing water is controlled so as to maintain the observed value of the transmittance within a certain range of, for example, 80–95%, preferably 91–94%. Here, the control of the temperature of the washing water is effected in such a manner that the temperature of the washing water will be lowered by a voluntary width, for example, 10° C., when the observed value of the transmittance exceeds over the upper limit of a preset range and will be elevated by a voluntary width, for example, 10° C., when it exceeds down the lower limit of the preset range.

The concentration of the impurities on the crystal is higher at a portion closer to the crystal surface and the amount of impurities eluted from the crystals will be greater as the temperature of the washing water is increased. Therefore, the amount of the impurities eluted out of the adhered mother liquor on the crystals into the washing water will be decreased by lowering the temperature of the washing water and, on the contrary, the amount of the impurities eluted out of the crystals into the washing water will be increased by elevating the temperature of the washing water, whereby the content of the impurities (the color components) in the purified terephthalic acid product will be maintained within a certain range.

By the technical measure of controlling the temperature of the washing water so as to maintain the transmittance of the purified terephthalic acid product within a certain range according to the present invention, it becomes possible to control the transmittance of the purified terephthalic acid product promptly by a simple procedure without altering the condition of oxidation of paraxylene, whereby a minute control can be realized and a purified product of terephthalic acid having a constant impurity level can be produced.

The Best Mode for Embodying the Invention

Below, the present invention will further be described by way of an embodiment with reference to appended FIG. 1.

FIG. 1 shows a flow sheet of an embodiment of the process for producing purified terephthalic acid according to the present invention. In FIG. 1, the numeral 1 represents a slurrying tank for slurrying the crystals of crude terephthalic acid (CTA) in water.

For producing a purified terephthalic acid product by the embodiment of FIG. 1, an aqueous slurry of crude terephthalic acid (CTA) is first prepared by introducing CTA 2 and water 3 into the CTA slurrying tank 1 with agitation. The resulting aqueous slurry is heated and pressurized to dissolve the crystals of CTA and the so-obtained aqueous solution 4 of terephthalic acid is supplied together with hydrogen gas 5 to the hydrogenation reactor 6, in order to subject the aqueous solution to a treatment by hydrogenation. The resulting reaction liquor 7 is cooled with relieving of the pressure, before it is transferred to a crystallization tank 8 to cause precipitation of terephthalic acid crystals there.

The slurry 9 of crystals formed in the crystallization tank 8 is forwarded to a solid/liquid separation unit 10 where the crystals are separated from the aqueous phase which is discharged out as waste liquor 11. In this manner, the impurities, such as paratoluic acid and color components, which are soluble in water can be removed from terephthalic acid crystals 12. The separated primarily purified terephthalic acid crystals 12 are then introduced into a TA re-slurrying tank 14 together with a washing water 13 (pure water) for re-slurrying therein. The resulting aqueous slurry 15 is introduced into another solid/liquid separation unit 16 where the purified terephthalic acid crystals are separated from the liquid phase which is returned as a recovered water 3 back to the CTA slurrying tank 1. The separated crystals 17 are dried in a TA dryer 18 to obtain a purified terephthalic acid (PTA) 19 as the final product.

During the above production procedure, a sample 20 of PTA is taken out of the TA dryer 18 and is forwarded to a transmittance observing unit 21 to determine the transmittance 22 thereof, which is introduced into a processing/control unit 23. In the processing/control unit 23, the observed value 22 of transmittance is compared with a preset value and, if the observed value 22 exceeds over the upper limit of the preset value, it puts out an output command signal 24 for lowering the temperature of the washing water by a decrement of, for example, 10° C., to a washing water temperature control unit 25 and, if the observed value 22 exceeds down the lower limit of the preset value, it puts out an output command signal 24 for elevating the temperature of the washing water by an increment of, for example, 10° C., to the temperature control unit 25.

The washing water temperature control unit 25 controls the temperature of the washing water 13 in accordance with the command signal 24 and the washing water of so-adjusted temperature is pumped into the TA re-slurrying tank 14. In this manner, the amount of the impurities eluted out of the crystals 12 into the washing water can be controlled, with the result of attainment of maintaining the level of transmittance and, thus, the content of impurities, especially of the color components, in the product PTA 19 within a certain range.

Now, the equation for the correlation between the temperature of the washing water and the PTA transmittance employed in the device for computing the controlling temperature width in the processing/control unit 23 will be described.

The correlation equation is established by a statistical method by taking the transmittance value, in %, of the PTA 19 discharged out of the TA dryer 18 as a variable y and the temperature of the washing water supplied to the TA re-slurrying tank 14, in ° C., as a variable x, respectively, based on the actually observed values of them. Here, the transmittance of PTA is represented by the value determined on a spectrophotometer using an aqueous solution of 2N KOH containing 15% by weight of PTA at a wave length of 340 nm (T-340) or 400 nm (T-400).

In general, for regression analysis assuming y as the objective variable and x as the explanatory variable, respectively, there are methods, for example, first-order regression analysis, multiple-order regression analysis and polynomial regression analysis. The accuracy of the analysis will be higher, in general, as the number of the order of regression analysis increases. Below, the result of an approximation using an equation by a first-order regression, which is easy in the processing, for the relationship between the transmittance of PTA by, as an example, T-340, and the temperature is given.

The regression coefficient (a) and the regression factor (b) determined by actual observations for the transmittance of PTA and the temperature of the washing water were 0.02 and 90, respectively. Here, the number of data (n) and the correlation coefficient (r) were 12 and 0.96, respectively.

Therefore, the correlation between the PTA transmittance y and the temperature of washing water x can be represented by $$y = a \cdot x + b$$

and therefore $$y = 0.02 \cdot x + 90 \tag{1}$$

Thus, it is seen from the number of data (n) and the correlation coefficient (r) that there is a correlation between the transmittance of PTA and the temperature of washing water. Namely, there is a positive correlation that an increase in the one value results in an increase in the other value.

From this, it is seen that an elevation of the temperature of washing water by an increment of 10° C. will result in an increase of the PTA transmittance T-340 by an increment of 0.2%.

While the above equation may not always be applicable, since the observed values may eventually vary due to the observation conditions, accuracy may be increased by incorporating periodical re-estimation. While the above results are based on an automatic control, similar controlling may be possible for a manual operation. While the above controlling technique is explained in a washing procedure by re-slurrying and solid/liquid separation, it is possible to employ a similar controlling technique also in other washing techniques including spraying of washing water onto crystal layer and a counter-flow contact of the washing water with the crystals.

By controlling the temperature of the washing water for washing the terephthalic acid crystals in accordance with the transmittance of the product crystals after the treatment by hydrogenation and crystallization, it is made possible to control the transmittance of the PTA product promptly by a simple procedure without necessitating alteration of the condition of oxidation of paraxylene, whereby a purified terephthalic acid having a low and constant level of impurity content can be produced.

Below, the present invention will further be described by way of Examples.

EXAMPLE 1

10 m$^3$ of a palladium catalyst supported on an activated carbon were placed as the hydrogenation catalyst in a hydrogenation reactor, whereto 60 t/hr of a crude terephthalic acid slurry containing 25% by weight of a crude terephthalic acid having a 4-CBA content of 0.36% by weight were supplied in order to carry out treatment by hydrogenation at a temperature of 280° C. under a partial pressure of hydrogen of 0.7 MPa, followed by a crystallization of terephthalic acid at a temperature of 100° C. under a pressure of 0.1 MPa (gauge) with subsequent solid/liquid separation of the resulting slurry of the crystals, whereupon the separated crystals were re-slurried in water so as to obtain a slurry of a concentration of 30% by weight, followed by a solid/liquid separation again with subsequent drying of the separated crystals to obtain a purified product of terephthalic acid. In this production system, the purified terephthalic acid product was observed for its transmittance and the process was controlled in such a manner that the temperature of the washing water was lowered by a decrement of 10° C. on exceeding the transmittance above a value of 93.5% and was elevated by a temperature increment of 10° C. on exceeding the transmittance below a value of 91.5%, whereby the T-340 was maintained within the range of 91–94%.

Comparative Example 1

In the production system of Example 1, the procedures were repeated except that the temperature of the washing water was maintained at a constant temperature of 100° C. It was found that the fluctuation of T-340 of the resulting purified terephthalic acid was in the range of 90–95%.

What is claimed is:

1. A process for producing purified terephthalic acid comprising hydrogenating a crude terephthalic acid obtained by a liquid phase oxidation of paraxylene in the presence of a hydrogenation catalyst, causing crystals of terephthalic acid to precipitate out of the hydrogenation reaction liquor, separating the resulting terephthalic acid crystals from the mother liquor, washing the separated crystals with water, observing the transmittance of the resulting purified terephthalic acid and controlling the temperature of the washing water so as to maintain the observed transmittance within a predetermined range.

2. A process as claimed in claim 1, wherein the washing of the separated crystals is realized by re-slurrying the crystals separated by a solid/liquid separation in the washing water to cause the impurities adhered on the crystals to be eluted out into the washing water and, then, separating the crystals in the resulting slurry by a solid/liquid separation.

3. A process as claimed in claim 1, wherein the washing of the separated crystals is realized by spraying the washing water onto a moving layer of the crystals separated by a solid/liquid separation so as to effect repeated re-slurrying and solid/liquid separation.

4. A process as claimed in claim 1, wherein the washing of the separated crystals is realized by replacing the reaction solvent with the washing water by bringing a moving layer of the crystals separated by a solid/liquid separation into contact with the washing water in a counter flow.

5. A process as claimed in claim 1, wherein the controlling of the temperature of the washing water is realized in such a manner that the temperature of the washing water is lowered when the observed transmittance value increases above the upper limit of a preset value and is elevated when the observed transmittance value decreases below the lower limit of the preset value.

6. A process as claimed in claim 1 wherein the controlling of the temperature of the washing water is realized in such a manner that the transmittance at a wave length of 340 nm or 400 nm is maintained within the range of 80–95%.

7. The process as claimed in claim 1, wherein the hydrogenation catalyst is selected from the group consisting of palladium, ruthenium, rhodium, osmium, iridium, platinum, platinum black, palladium black, iron and cobalt-nickel.

8. The process as claimed in claim 1, wherein the catalyst is supported on a carrier.

9. The process as claimed in claim 1, wherein the hydrogenation occurs at a temperature of at least 230° C., under a pressure of 1–11 MPa, and at a hydrogen partial pressure of at least 0.05 MPa.

10. The process as claimed in claim 6, wherein the transmittance is maintained within the range of 91–94%.

* * * * *